(12) United States Patent
Omori et al.

(10) Patent No.: US 8,162,152 B2
(45) Date of Patent: Apr. 24, 2012

(54) BLOOD FILTER DEVICE AND METHOD OF MANUFACTURING THE SAME

(75) Inventors: Masayoshi Omori, Hiroshima (JP); Shota Nakao, Hiroshima (JP); Yutaka Katsuno, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 660 days.

(21) Appl. No.: 12/083,139

(22) PCT Filed: Jul. 26, 2006

(86) PCT No.: PCT/JP2006/314776
§ 371 (c)(1), (2), (4) Date: Apr. 4, 2008

(87) PCT Pub. No.: WO2007/039977
PCT Pub. Date: Apr. 12, 2007

(65) Prior Publication Data
US 2009/0045131 A1    Feb. 19, 2009

(30) Foreign Application Priority Data

Oct. 4, 2005  (JP) ................. 2005-291205

(51) Int. Cl.
*B01D 35/30*  (2006.01)
*B01D 35/00*  (2006.01)
*B01D 29/00*  (2006.01)
*B01D 29/07*  (2006.01)
*B29C 65/00*  (2006.01)

(52) U.S. Cl. .................. 210/451; 210/232; 210/321.77; 210/321.86; 210/471; 210/436; 210/445; 210/453; 210/454; 210/455; 210/479; 210/493.1; 210/493.5; 156/60

(58) Field of Classification Search ............... 210/493.1, 210/493.5
See application file for complete search history.

(56) References Cited

U.S. PATENT DOCUMENTS 3,873,288 A * 3/1975 Wachter et al. ................. 55/497
(Continued)

FOREIGN PATENT DOCUMENTS

JP         55-169459        6/1982
(Continued)

*Primary Examiner* — Benjamin Kurtz
(74) *Attorney, Agent, or Firm* — Hamre, Schumann, Mueller & Larson P.C.

(57) ABSTRACT

A blood filter device includes: a housing that includes a dome 2 provided with a blood inlet, a filter retaining portion 3 that is positioned below the dome, and a bottom portion 4 provided with a blood outlet; and a filter 8 that is mounted in a cavity of the filter retaining portion and partitions a cavity of the housing into a dome side and a bottom portion side. A sheet-like filter member 8a of the filter forms a plurality of pleats, and ridgelines of the respective pleats traverse the filter retaining portion in parallel respectively. The blood filter device further includes an annular holder 9 intervening between the filter retaining portion and the filter, a annular rib substrate 10 that is disposed facing the ridgelines of the pleats in an outer peripheral region of the filter and has a plurality of ribs inserted respectively between the ridgelines of the plurality of pleats; and a bonding resin 11 that is charged into outer peripheral portions of the filter including the annular holder and the annular rib substrate, and bonds the outer peripheral portion of the filter to the filter retaining portion. Gaps are ensured between the plurality of pleats of the filter, and thus air bubbles can be removed easily.

7 Claims, 12 Drawing Sheets

U.S. PATENT DOCUMENTS

| | | | |
|---|---|---|---|
| 5,178,760 A | 1/1993 | Solberg, Jr. | |
| 5,273,560 A * | 12/1993 | Kadoya et al. | 55/498 |
| 5,618,425 A | 4/1997 | Mitamura et al. | |
| 5,651,765 A | 7/1997 | Haworth et al. | |
| 6,074,450 A * | 6/2000 | Raber | 55/497 |
| 6,143,174 A | 11/2000 | Graus | |
| 6,319,300 B1 * | 11/2001 | Chen | 55/497 |
| 2006/0191841 A1 | 8/2006 | Kawarabata et al. | |

FOREIGN PATENT DOCUMENTS

| | | |
|---|---|---|
| JP | 57-95223 | 6/1982 |
| JP | 4-310202 A | 11/1992 |
| JP | 9-508564 A | 9/1997 |
| JP | 10-211411 A | 8/1998 |
| JP | 2000-517240 A | 12/2000 |
| JP | 3270193 | 1/2002 |
| WO | WO 2004/084974 A1 | 10/2004 |

* cited by examiner

BLOOD FILTER DEVICE AND METHOD OF MANUFACTURING THE SAME

TECHNICAL FIELD

The present invention relates to a blood filter device used for filtering foreign substances, thrombi, and the like in an artificial heart-lung circuit. In particular, the present invention relates to a blood filter device configured so that air bubbles remaining in a filter can be removed easily and to a method of manufacturing the same.

BACKGROUND ART

In many cases, a blood filter device such as an arterial filter is incorporated in an artificial heart-lung circuit used for heart surgery involving extracorporeal circulation for the sake of safety. To provide security for patients, it has been demanded strongly that such a blood filter device be configured so that it can remove minute foreign substances in the artificial heart-lung circuit, thrombi formed during operation, or air that has entered or been released from the circuit so as not to allow them to enter the patient body.

A filter generally used in the blood filter device is a polyester screen filter with pores of about 20 to 40 μm that has been pleated and then formed into a cylindrical shape. For example, Patent Document 1 discloses that a filter sheet is folded so as to have a plurality of pleats and the pleated filter member then is formed into a cylindrical shape in which the respective pleats are arranged radially with peaks thereof positioned on the outer circumference side and valleys thereof positioned on the inner circumference side. The thus-formed cylindrical filter is disposed in a cylindrical housing. In the filter configured as above, blood flows in the housing in the radial direction of the cylindrical filter member to pass therethrough, which allows therethrough, which allows dirt, impurities, thrombi, and the like contained in the blood to be removed effectively.

In the filter as described above, blood first flows into an upper part of the cylindrical filter member, passes through the cylindrical filter member in its radial direction via an outer part of the filter member, and then flows out from a lower part of the cylindrical filter member via an inner part of the filter member. In this filter, the filter member surface extends vertically. This poses a problem in that, when a priming solution flows into the filter surface during a priming operation, air bubbles are liable to remain in the filter. Moreover, it is difficult to discharge the remaining air bubbles to the outside. This is because, since the filter member surface extends vertically, the air bubbles cannot be released from the filter easily, so that it takes quite a long time to remove the air bubbles completely.

More specifically, air bubbles remaining in the filter can be released with an impact from the outside caused by, for instance, flicking the housing with a finger. In this case, however, although the air bubbles can be released temporarily by giving an impact from a portion close to a position where the air bubbles adhere, they are liable to adhere again to an adjacent pleat of the filter. Thus, it is difficult to bring the air bubbles to an air vent provided above.

Patent Document 2 describes a blood filter device that solves such problems, and it is configured so that impurities, thrombi, and the like in blood can be removed effectively, and air bubbles remaining in a filter also can be removed easily.

The blood filter device described in Patent Document 2 includes a housing that includes a dome provided with a blood inlet and an air vent at the top of the dome, a filter retaining portion disposed below the dome, and a bottom portion that is disposed below the filter retaining portion and is provided with a blood outlet. Blood that has flowed into the dome from the inlet passes through the filter retaining portion, and flows out from the outlet. A filter is disposed in the filter retaining portion so as to partition a cavity of the housing into a dome side and a bottom portion side. The filter is formed of a sheet-like filter member folded to have a plurality of pleats, and it is disposed so that ridgelines of the plurality of pleats traverse respectively the cavity of the filter retaining portion in parallel.

According to this configuration, foreign substances, thrombi, and the like in blood can be removed reliably, and since there are no obstacles in the vertical direction of the filter, air bubbles adhered onto the top face of the filter during a priming operation can be removed easily by only applying a physical impact to the housing.

Patent Document 1: Japanese Patent No. 3270193
Patent Document 2: WO2004/084974

DISCLOSURE OF INVENTION

Problem to be Solved by the Invention

As described above, it is desirable that the filter shaped by arranging a plurality of pleats in parallel is retained in the filter retaining portion in the state where there is a certain gap between adjacent pleats. When the pleats are in contact with each other, and there is no gap therebetween, a blocked space is formed at the bottom of a valley between the pleats. Therefore, if air bubbles remaining in or air bubbles formed at another places get trapped in the blocked space, it is difficult to remove the air bubbles even by applying a physical impact to the housing.

However, it is also difficult to fix the filter in the cavity of the filter retaining portion while maintaining a gap between adjacent pleats. That is, when disposing the filter that is folded to have pleats in the filter retaining portion, the pleats bulge because the sheet-like filter member forming the filter is in a free state. Thus, adjacent pleats are liable to be in contact with each other. This can be a problem especially when the efficiency of filtering is to be increased without increasing the size of the housing of the filter. That is, if the pleats are heightened and pitches are reduced to increase the area of a filter film, the pleats are liable to be in contact with each other with their natural bulges.

With forgoing in mind, it is an object of the present invention to provide a blood filter device configured so that gaps between a plurality of pleats of a sheet-like filter member forming a filter are ensured to remove air bubbles easily.

Means for Solving Problem

A blood filter device of the present invention includes: a housing including a dome that is provided with a blood inlet and forms an upper part of the housing, a filter retaining portion that is positioned below the dome and forms a middle part of the housing, and a bottom portion that is disposed below the filter retaining portion and is provided with a blood outlet; and a filter that is disposed in a cavity of the filter retaining portion and partitions a cavity of the housing into a dome side and a bottom portion side. The filter is formed of a sheet-like filter member folded to have a plurality of pleats, and is disposed so that ridgelines of the plurality of pleats traverse respectively the cavity of the filter retaining portion in parallel.

In order to solve the above problems, the blood filter device of the present invention includes: an annular holder disposed to intervene between an inner peripheral surface of the filter retaining portion and an outer peripheral surface of the filter; an annular rib substrate, which is an annular member disposed facing the ridgelines of the plurality of pleats in an outer peripheral region of the filter and is provided with a plurality of ribs that are inserted respectively between the ridgelines of the plurality of pleats; and a bonding resin that is charged in an outer peripheral portion of the filter including the annular holder and the annular rib substrate and bonds the outer peripheral portion of the filter to the filter retaining portion.

In order to manufacture the blood filter device as described above, a method of manufacturing the blood filter device of the present invention includes steps of: mounting the filter in an annular holder formed so as to intervene between an inner peripheral surface of the filter retaining portion and an outer peripheral surface of the filter, so that the outer peripheral surface of the filter faces the inner peripheral surface of the annular holder; mounting an annular rib substrate, which is an annular member having a shape and a size to face ridgelines of the plurality of pleats in an outer peripheral region of the filter and is provided with a plurality of ribs that can be inserted respectively between the ridgelines of the plurality of pleats, on the filter so as to insert respectively the plurality of ribs between the ridgelines of the plurality of pleats and forming a filter structure in which the filter, the annular holder, and the annular rib substrates are combined; placing the filter structure in a cavity of the filter retaining portion and mounting thereof in the housing; and charging a bonding resin into an outer peripheral portion of the filter including the annular holder and the annular rib substrate and hardening the bonding resin to bond the filter to the filter retaining portion with the bonding resin.

According to the blood filter device configured as above, since the plurality of ribs provided on the annular rib substrate are inserted respectively between the ridgelines of the plurality of pleats, gaps between the plurality of pleats of the filter are ensured. As the result, air bubbles remaining in the filter or air bubbles trapped in the filter are removed easily.

Figure 1A:
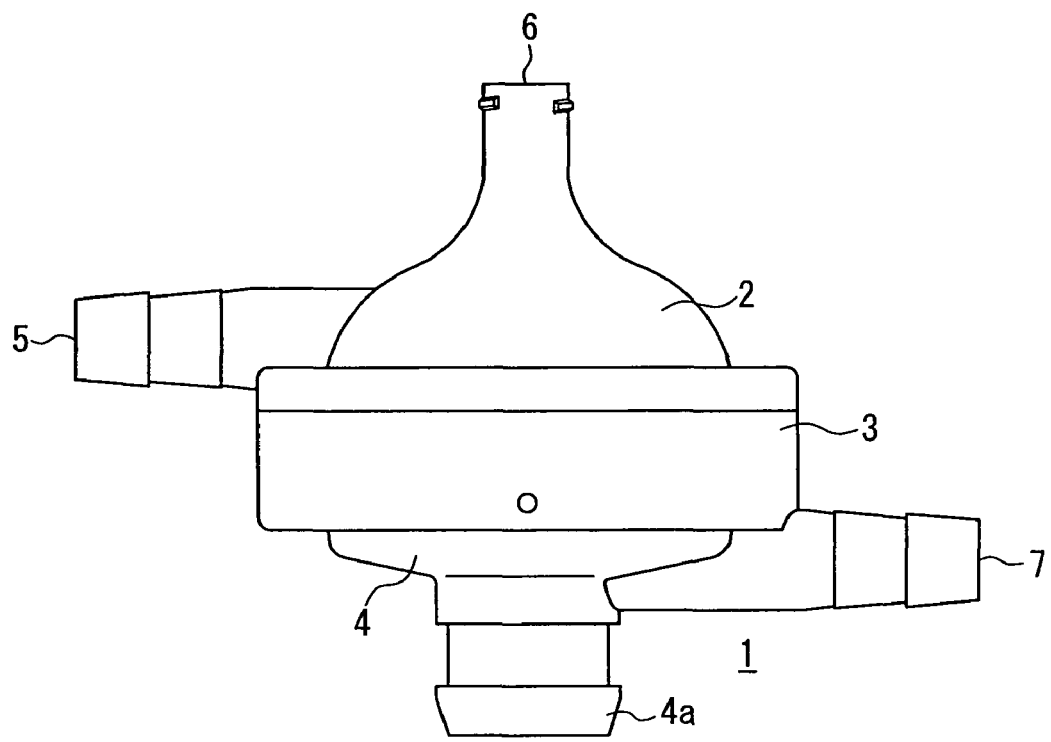
FIG. 1A is a front view of a blood filter device according to an embodiment of the present invention.

DESCRIPTION OF REFERENCE NUMERALS 1 housing
1a upper half of housing
1b lower half of housing
2 dome
3 filter retaining portion
3a retaining portion inner cylinder
3b retaining portion outer cylinder
4 bottom portion
4a support portion
5 blood inlet
6 air vent
7 blood outlet
8 filter
8a sheet-like filter member
8b pleat
8c pleat gap
9 annular holder
9a cylinder portion
9b flange portion
10 annular rib substrate
10a annular portion
10b rib
10c pleat receiving portion
11 bonding resin
12 filter structure
13 auxiliary bonding resin
14 notch
15 through hole
16 rotating jig
16a cavity
17 resin reservoir
18 resin supply channel

DESCRIPTION OF THE INVENTION

In the blood filter device of the present invention, it is preferable that an outer periphery of the filter is bonded to an inner peripheral surface of the annular holder with an auxiliary bonding resin, and it is further bonded to the filter retaining portion with the bonding resin.

Further, it is preferable that the blood filter device of the present invention includes a pair of the annular rib substrates, and the annular rib substrates are disposed facing the ridgelines of the plurality of pleats on both top and bottom surfaces of the filter respectively.

In the method of manufacturing the blood filter device of the present invention, it is preferable that after mounting the filter in the annular holder, an auxiliary resin is charged into outer peripheral portions of the filter so as to retain the outer peripheral portion of the filter to the inner peripheral surface of the annular holder with the auxiliary bonding resin.

Furthermore, it is preferable that after mounting the filter structure in the housing, the bonding resin is charged into an outer peripheral region of the filter including the annular holder and the annular rib substrates while applying a centrifugal force about the central axis of the cavity of the filter holder.

Hereinafter, a blood filter device according to an embodiment of the present invention will be described with reference to the drawings.

Figure 1B:
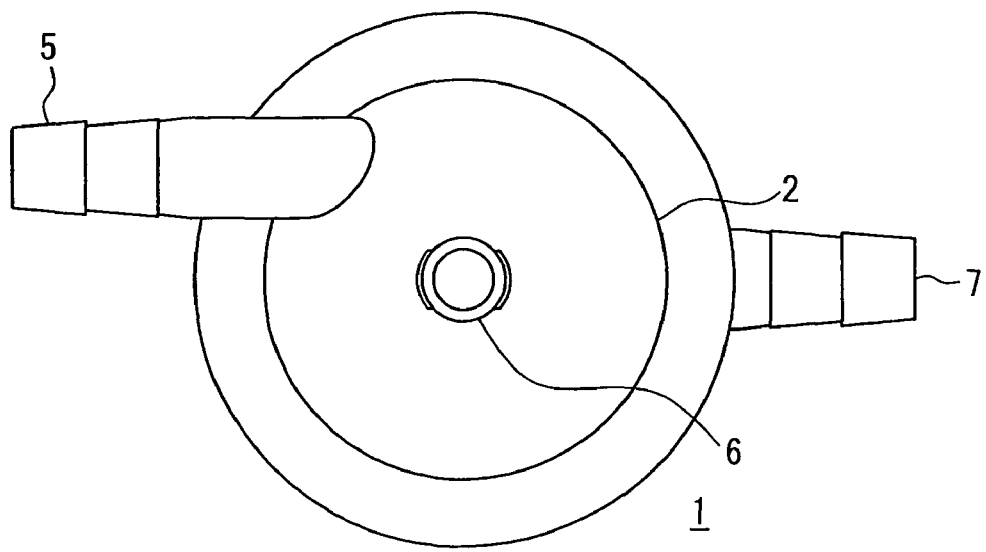
FIG. 1B is a plan view of the blood filter device.
Figure 1C:
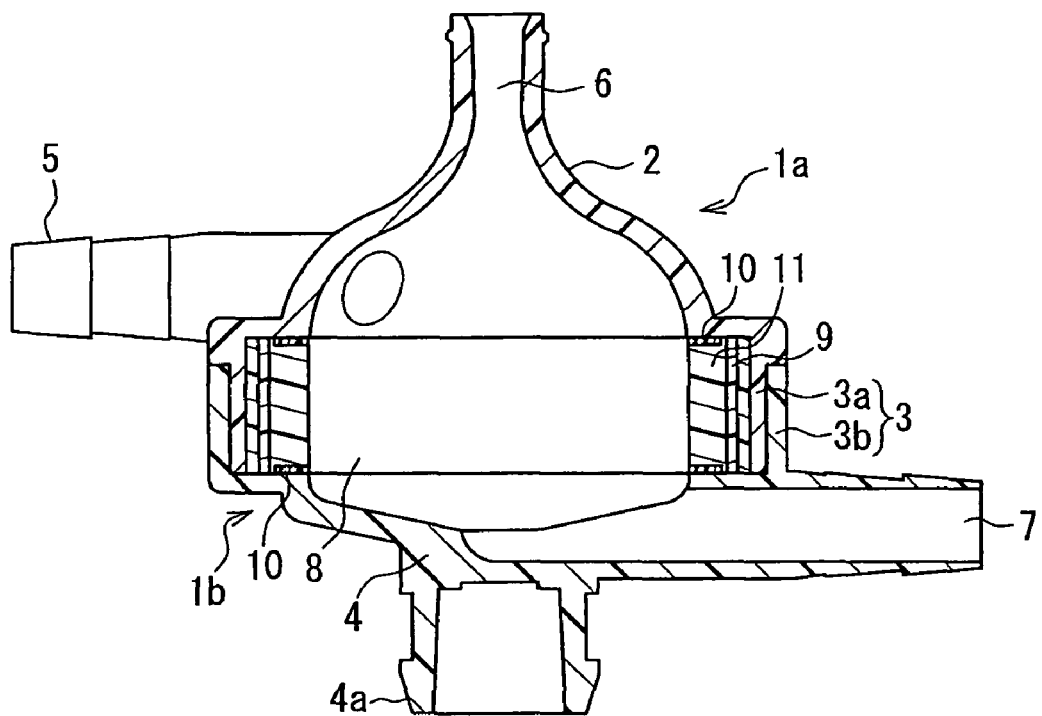
FIG. 1C is a cross-sectional view of the blood filter device.

FIG. 1A is a front view of the blood filter device, FIG. 1B is a plan view of the same, and FIG. 1C is a cross-sectional view of the same. A housing 1 is made of resin for example, and it includes a dome 2 forming an upper part of the housing, a filter retaining portion 3 forming a middle part of the housing, and a bottom portion 4 forming a lower part of the housing. The housing 1 has a horizontal cross section of a circular shape.

On a lateral portion of the dome 2, a blood inlet 5 is provided so as to allow blood to flow into the dome 2 horizontally and along an inner wall of the dome 2. On the top of the dome 2, an air vent 6 for discharging air such as air bubbles is provided. A blood outlet 7 is provided on the bottom portion 4. A filter retaining portion 3 has a cylindrical shape. As shown in FIG. 1C, a filter 8 for filtering foreign substances in blood is disposed in the filter retaining portion 3. The filter 8 partitions a cavity of the housing 1 into a dome 2 side and a bottom portion 4 side. Liquid that has flowed into the dome 2 from the blood inlet 5 passes through the filter retaining portion 3 and then flows out from the blood outlet 7. The bottom portion 4 also has a support portion 4a, which is used when installing the filter device and is irrelevant to the filtering function.

The dome 2 is formed so that an inner diameter thereof is reduced gradually toward the top of the dome 2. This allows air bubbles to be gathered and released to move upward along the inner peripheral surface of the dome 2. The dome 2 has a circular cross section, and is provided with the blood inlet 5 so as to allow blood flow into the dome horizontally and along an inner wall of the dome 2. The blood that has flowed in from the blood inlet 5 flows downwards, and then flows into the filter retaining portion 3. The shape of the dome 2 is not limited to that shown in FIG. 1A etc. as long as it is formed so that an outer diameter thereof is reduced toward the air vent 6. For instance, it may have a conical shape or a funnel shape.

As shown in FIG. 1C, the housing 1 is composed of an upper half 1a and a lower half 1b of the housing. The filter retaining portion 3 is composed of a retaining portion inner cylinder 3a and a retaining portion outer cylinder 3b formed in the upper half 1a and the lower half 1b of the housing respectively. The upper half 1a and the lower half 1b of the housing are joined together by fitting the retaining portion outer cylinder 3b into the retaining portion inner cylinder 3a, thereby obtaining the housing 1 as a single component.

Figure 2:
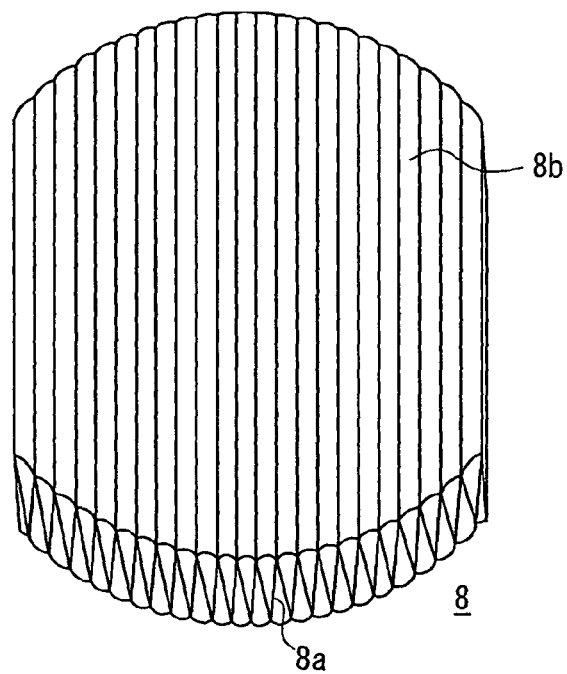
FIG. 2 is a perspective view of a filter constituting the blood filter device.

As schematically shown in FIG. 2, the filter 8 is formed of a sheet-like filter member 8a made of a sheet-like mesh material folded so as to form a plurality of pleats. The filter 8 is disposed so that ridgelines 8b of the plurality of pleats traverse respectively a cavity of the retaining portion inner cylinder 3a (filter retaining portion 3) in parallel. That is, the ridgelines 8b of the respective pleats are parallel to the direction of the blood inlet 5 or the blood outlet 7, and is oriented in the direction along a chord of the retaining portion inner cylinder 3a. An enveloping surface of the ridgelines 8b of the respective pleats is flat, and thus the filter 8 as a whole has a flat outer shape. By disposing the ridgelines 8b of the respective pleats in parallel to the direction of the blood inlet 5 or the blood outlet 7, a flow of blood or a priming solution becomes parallel to the ridgelines 8b of the pleats, thereby those solutions flow easily into spaces between the pleats. As the result, removal of air bubbles is ensured.

As shown in FIG. 1C, the annular holder 9 is disposed to intervene between an inner peripheral surface of the filter retaining portion 3 and an outer peripheral surface of the filter 8. An annular rib substrate 10 is disposed facing the ridgelines 8b of the plurality of pleats of the filter 8 in an outer peripheral region of the filter 8. As will be described below, the annular rib substrate 10 has a plurality of ribs (not shown in FIG. 1C) that are inserted respectively between the ridgelines 8b of the plurality of pleats. A bonding resin 11 is charged into an outer peripheral portion of the filter 8 including the annular holder 9 and the annular rib substrate 10. The filter 8 is bonded to the inner peripheral surface of the annular holder 9 with an auxiliary boding resin (not shown), and it is bonded further to the inner peripheral surface of the filter retaining portion 3, namely the inner peripheral surface of the retaining portion inner cylinder 3a, with the bonding resin 11.

Figure 3:
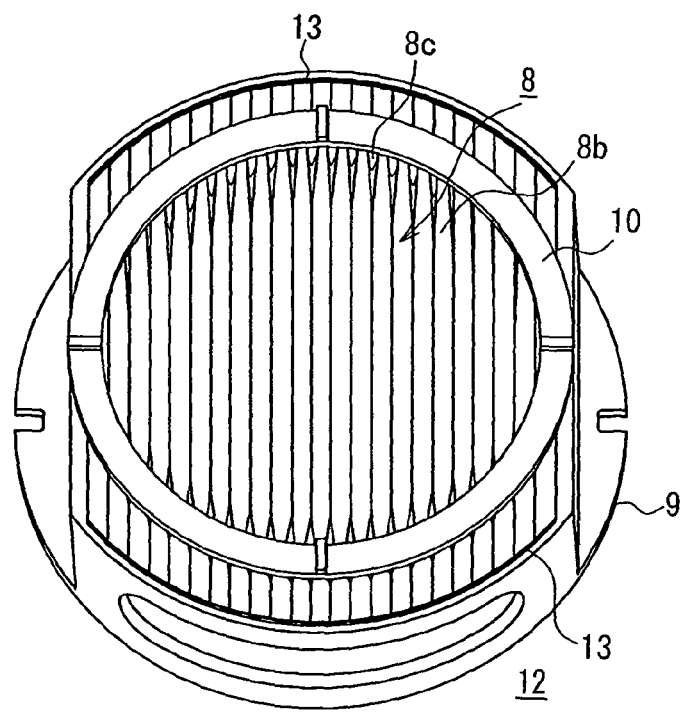
FIG. 3 is a perspective view of a filter structure constituting the blood filter device.

FIG. 3 shows a filter structure 12 in which the filter 8, the annular holder 9, and the annular rib substrate 10 are combined. The outer periphery of the filter 8 is bonded to the inner peripheral surface of the annular holder 9 with an auxiliary bonding resin 13.

Figure 4:
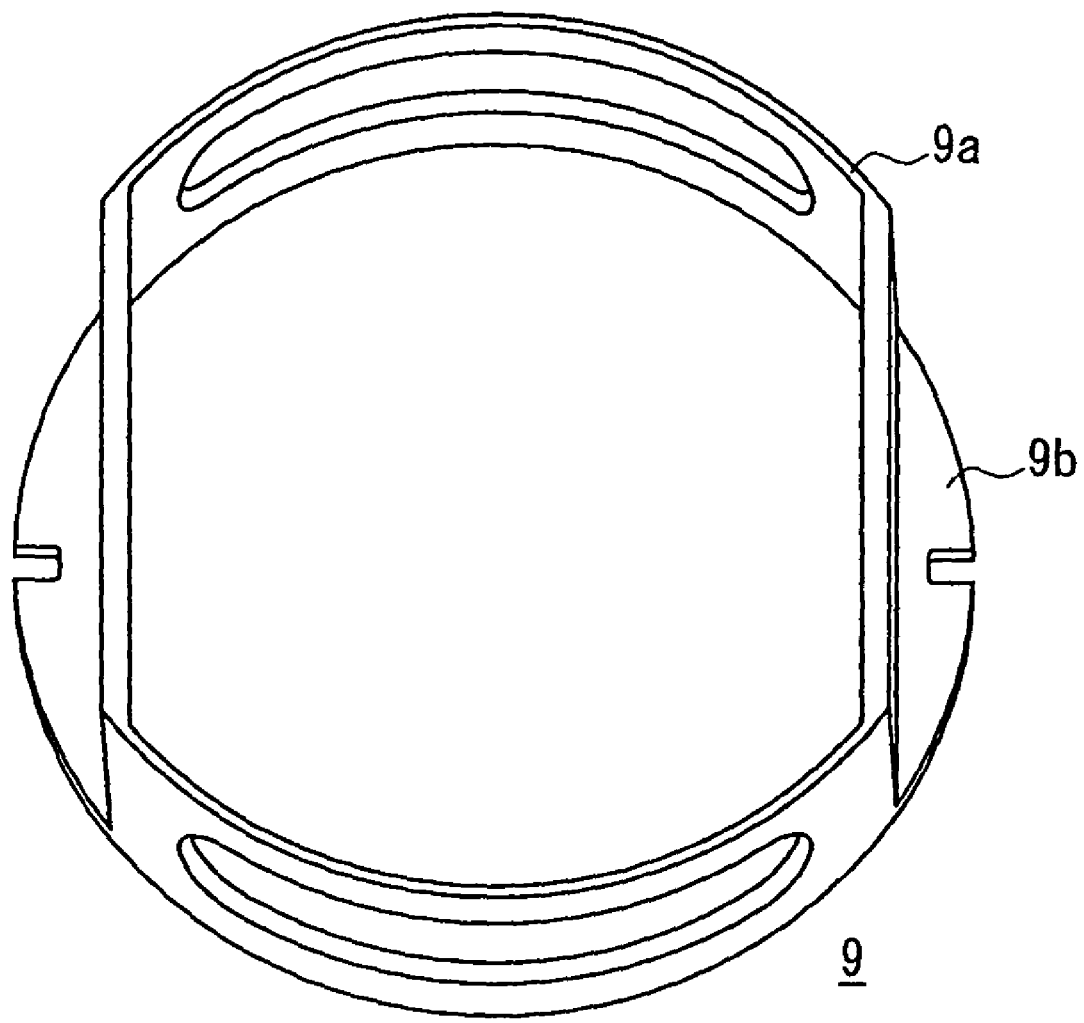
FIG. 4 is a perspective view of an annular holder constituting the blood filter device.
Figure 5A:
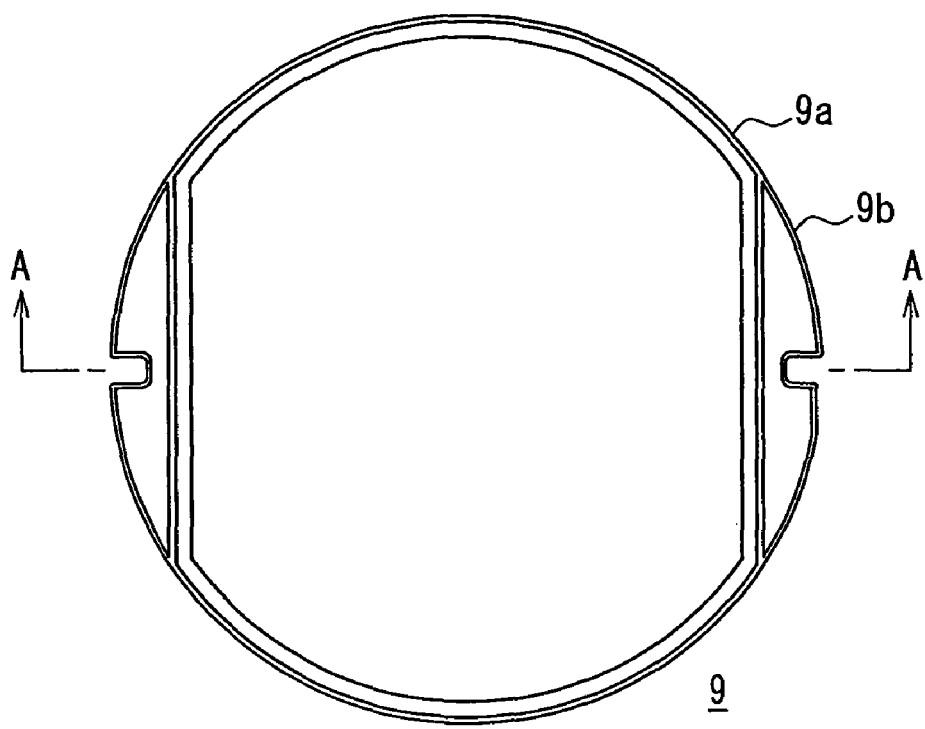
FIG. 5A is a plan view of the annular holder.
Figure 5B:
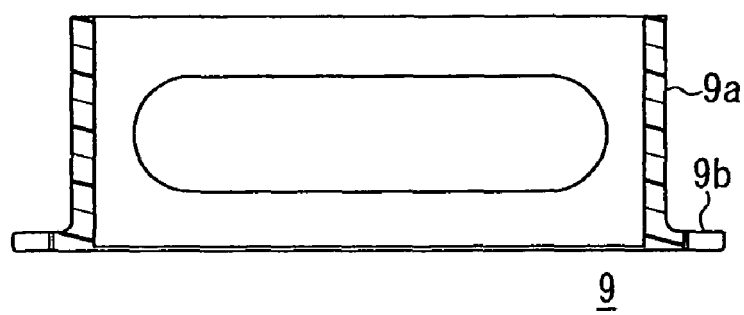
FIG. 5B is a cross-sectional view of the annular holder.

FIGS. 4, 5A, and 5B show the structure of the annular holder 9. FIG. 4 is a perspective view of the annular holder 9, FIG. 5A is a plan view of the same, and FIG. 5B is a cross-sectional view of the same along the A-A line in FIG. 5A. The annular holder 9 is composed of a cylinder portion 9a and a flange portion 9b. The cylinder portion 9a provides an inner space in which the filter 8 is mounted and an inner peripheral surface to which the outer peripheral surface of the filter 8 is bonded. The flange portion 9b retains the annular holder 9 when mounting the filter 8 and the annular rib substrate 10, and also provides convenience in handing when mounting the filter structure 12 into the filter retaining portion 3.

Figure 6:
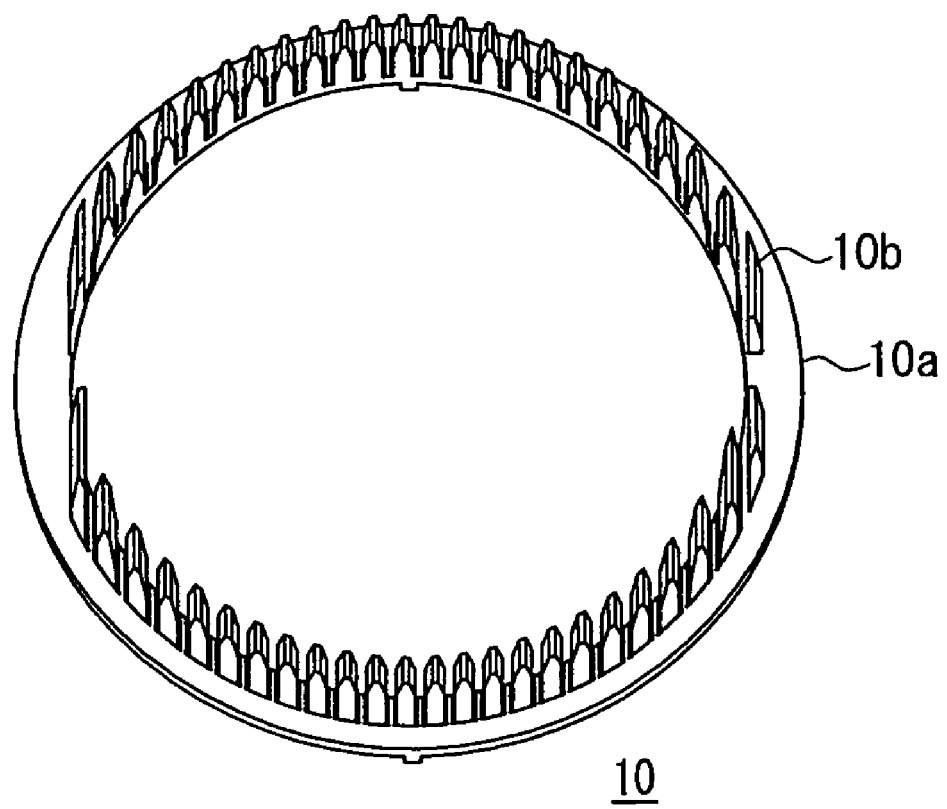
FIG. 6 is a perspective view of an annular rib substrate constituting the blood filter device.
Figure 7A:
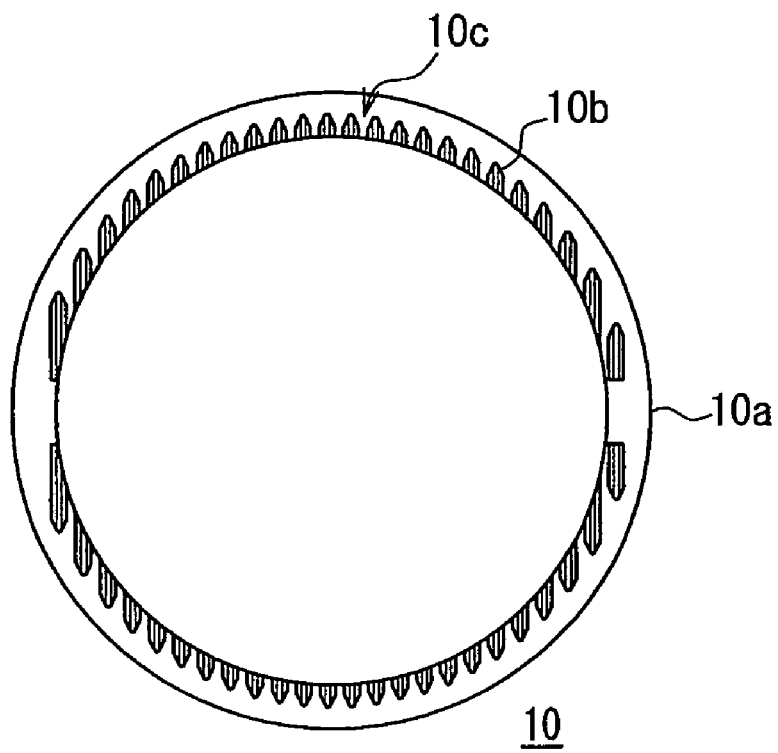
FIG. 7A is a plan view of the annular rib substrate.
Figure 7B:
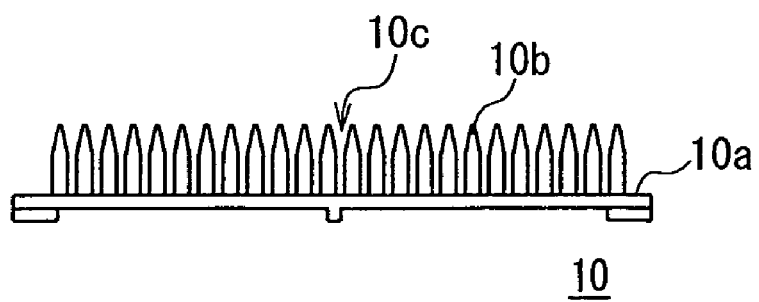
FIG. 7B is a front view of the annular rib substrate.

FIGS. 6, 7A, and 7B show the structure of the annular rib substrate 10. FIG. 6 is a perspective view of the annular rib substrate 10, FIG. 7A is a plan view of the same, and FIG. 7B is a front view of the same. The annular rib substrate 10 is composed of an annular portion 10a having a disc shape and a plurality of ribs 10b. The plurality of ribs 10b are aligned on a surface of the annular portion 10a, and the ribs 10b forming a pair of upper and lower ribs in FIG. 7A correspond respectively to spaces between the ridgelines 8b of the pleats of the filter 8. Thus, respective pleat receiving portions 10c formed by gaps between adjacent ribs 10b correspond to the ridgelines 8b of the respective pleats. In the filter structure 12 shown in FIG. 3, the ridgelines 8b are inserted respectively in the pleat receiving portions 10c.

As shown in FIG. 3, by mounting the annular rib substrate 10, in the outer peripheral region of the filter 8, gaps of the sheet-like filter member 8a forming the respective pleats are widened by the ribs 10b, thereby forming pleat gaps 8c.

The filter structure 12 configured as above is mounted in the filter retaining portion 3 as shown in FIG. 1C, and are bonded together with the bonding resin 11, thereby forming the blood filter device of the present embodiment.

In the blood filter device of the present invention configured as above, since the pleat gaps 8c are formed in the peripheral region of the filter 8, air bubbles or the like remaining in spaces between the pleats of the filter 8 move upward through the pleat gaps 8c, and are more likely to be removed. Blood or a priming solution from the blood inlet 5 flows through the pleat gaps 8c of the peripheral region and flows smoothly between the pleats when passing through the filter 8 of the filter retaining portion 3. By this flow, air bubbles are removed easily. Furthermore, in some cases, gaps of the sheet-like filter member 8a are widened by the initial flow, and the pleat gaps are formed even in a central region of the filter 8, thereby widening the channel of the priming solution. Accordingly, if the pleat gaps 8c are formed by the annular substrate 10 in at least a peripheral region of the filter 8, the sufficient function for removing air bubbles remaining or trapped in the filter 8 can be provided.

By mounting the annular rib substrate 10 at least on the top surface of the filter 8, a sufficient effect in practical use is obtained. If a pair of the annular rib substrates 10 are mounted respectively on both the top and bottom surfaces of the filter 8, air bubbles can be removed more easily.

As the filter member, a mesh material, a woven material, a non-woven material, or the like or a combination thereof can be used. The filter member can be made of polyester, polypropylene, polyamide, fluorocarbon fiber, stainless steel or the like.

It is preferable that the housing 1, especially a horizontal cross section of the dome 2, has a circular shape. However, it is to be noted here that other shapes such as an ellipse shape also can produce the same effect as described above.

Figure 8A:
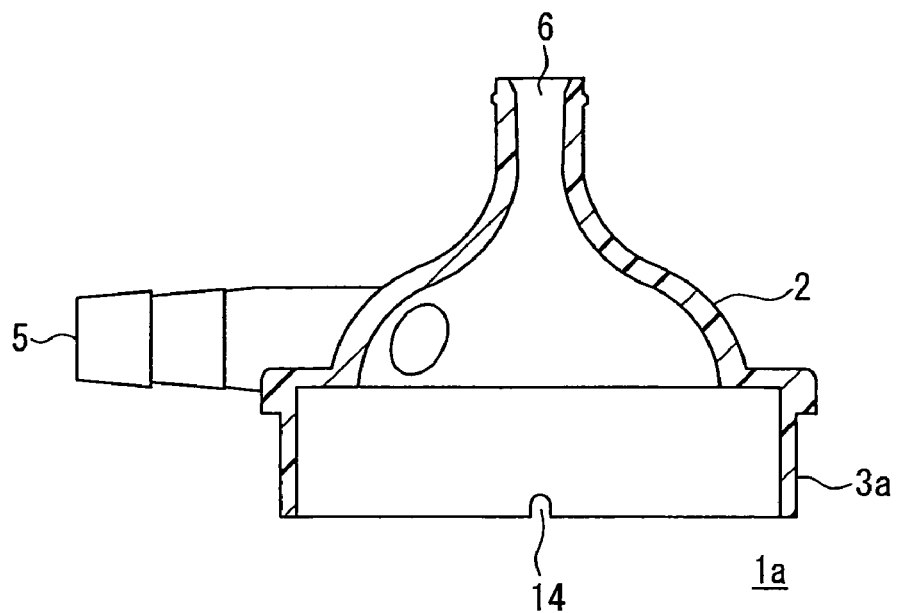
FIG. 8A is a cross-sectional view of an upper half of housing constituting the blood filter device.
Figure 8B:
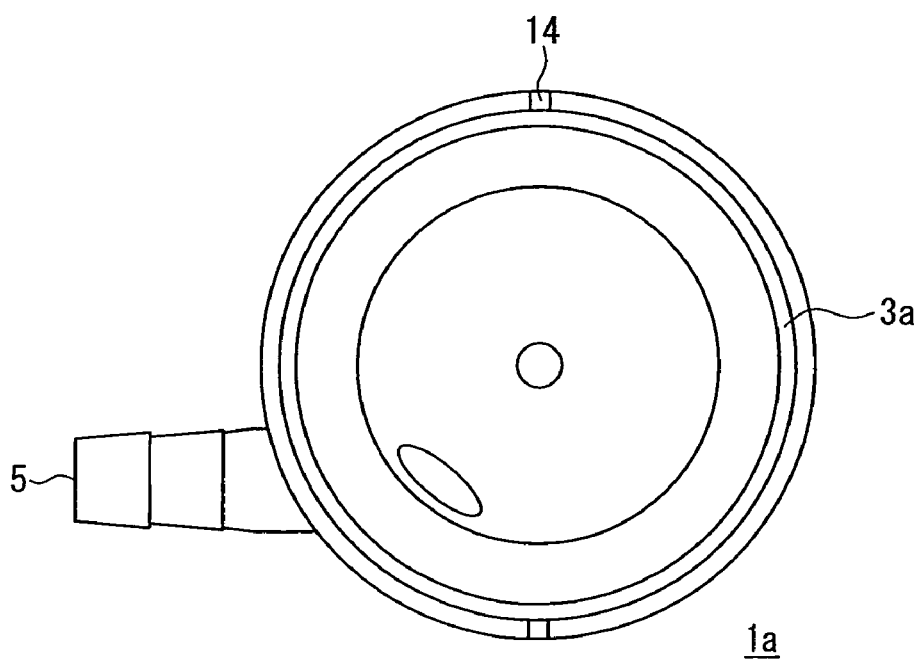
FIG. 8B is a bottom view of the upper half of the housing.
Figure 9A:
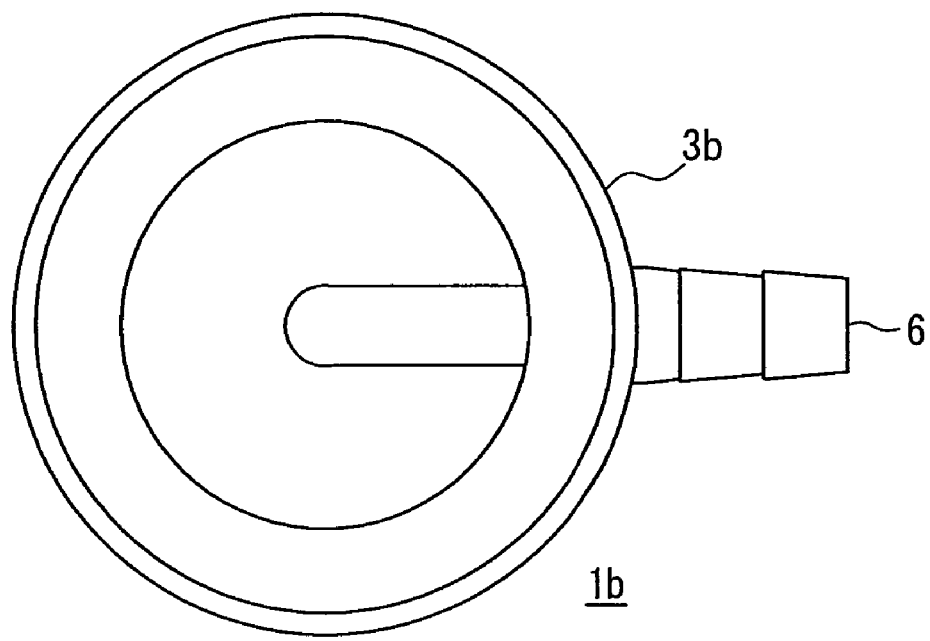
FIG. 9A is a plan view of a lower half of the housing.
Figure 9B:
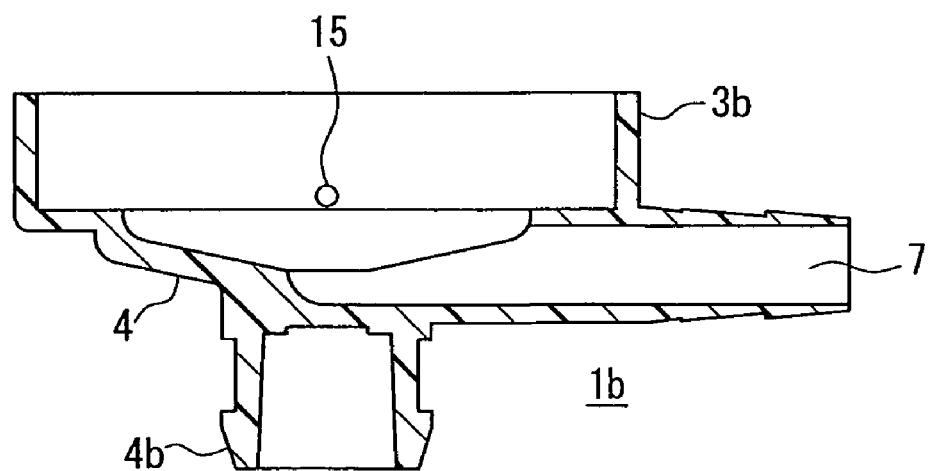
FIG. 9B is a cross-sectional view of the lower half of the housing.

Next, a method of manufacturing the blood filter device according to the present embodiment will be described. FIG. 8A is a cross-sectional view of the upper half 1a of the housing constituting the blood filter device, and FIG. 8B is a bottom view of the same. FIG. 9A is a plan view of the lower half 1b of the housing, and FIG. 9B is a cross-sectional view of the same.

The basic configuration is as described with reference to FIGS. 1A-1C. A pair of notches 14 are formed on the retaining portion inner cylinder 3a of the upper half 1a of the housing. Through holes 15 are formed on the retaining portion outer cylinder 3b of the lower half 1b of the housing, at the positions corresponding to the pair of notches 14 on the retaining portion inner cylinder 3a. When the upper half 1a of the housing is fit into the lower half 1b of the housing, the notches 14 communicate with the through holes 15, thereby forming holes that pass through peripheral walls of the retaining portion inner and outer cylinders 3a and 3b. These holes are used as resin paths for charging a resin during potting, which will be described below.

Figure 10:
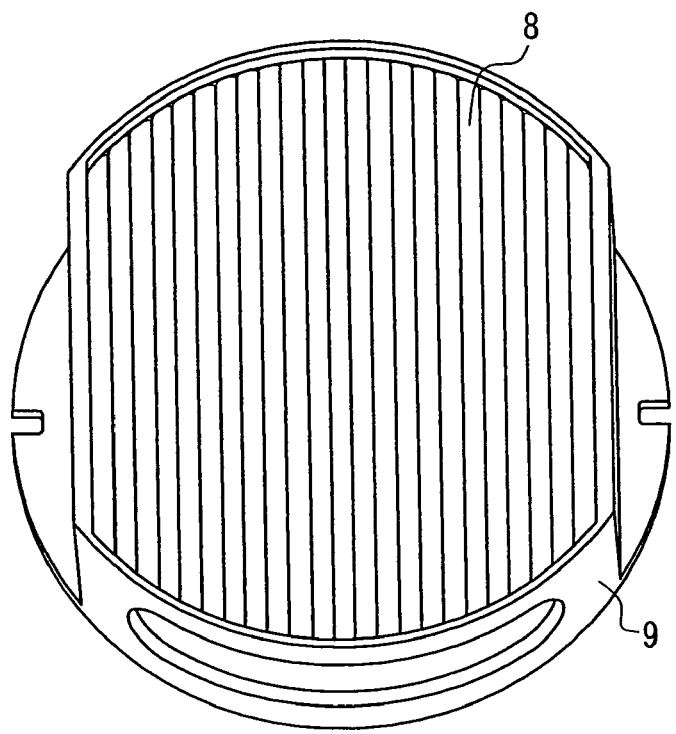
FIG. 10 is a perspective view showing a process in a method of manufacturing the blood filter device according to an embodiment of the present invention.
Figure 11:
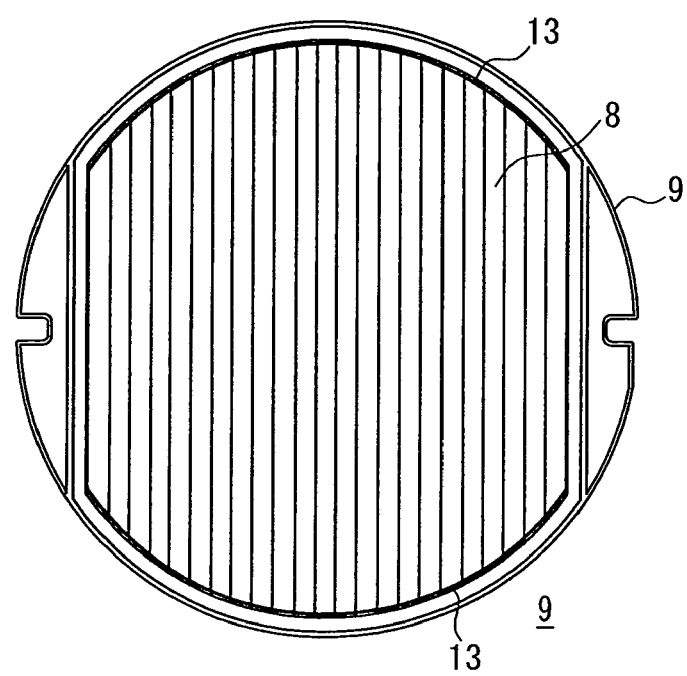
FIG. 11 is a plan view showing another process in the manufacturing method.
Figure 12:
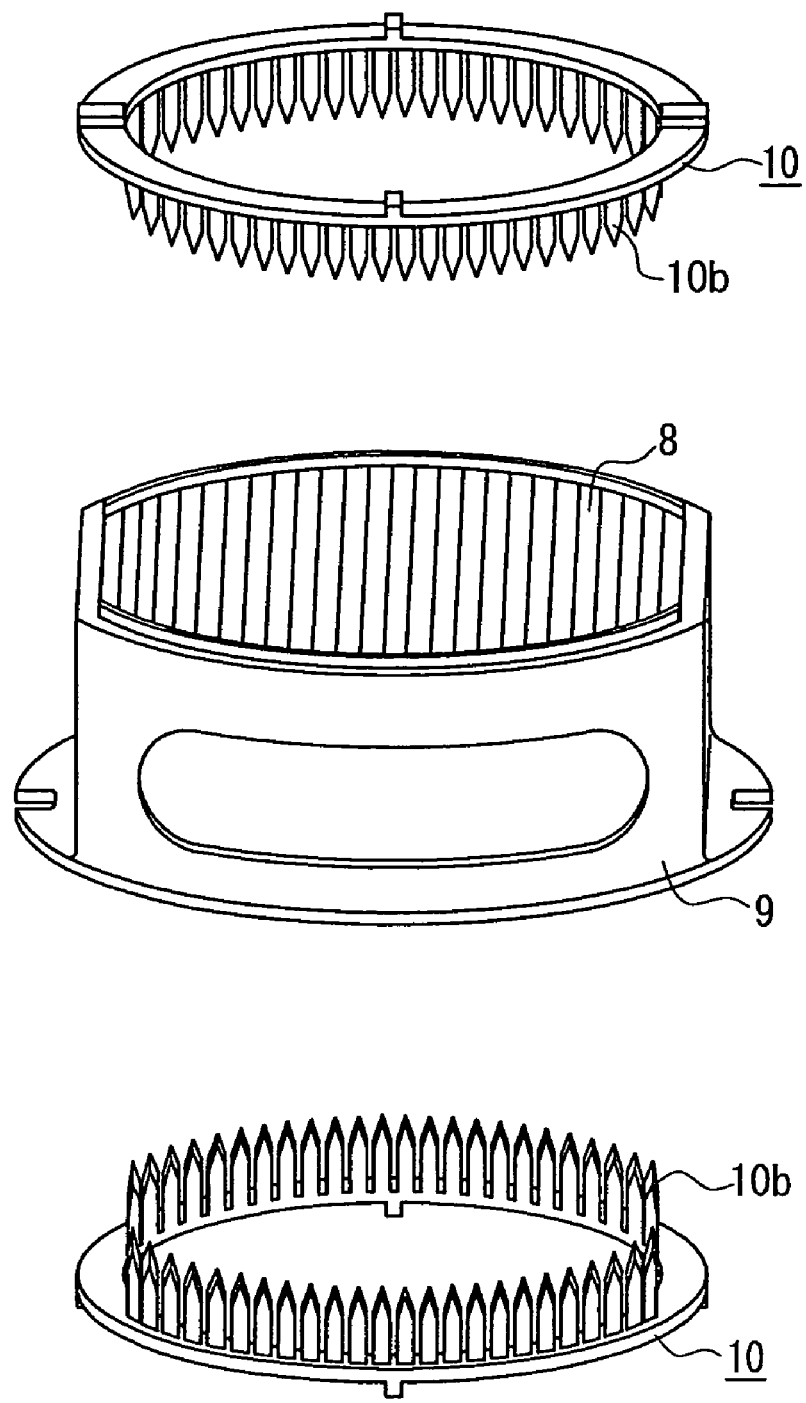
FIG. 12 is a perspective view showing yet another process in the manufacturing method.

FIGS. 10, 11, and 12 show processes relating to the manufacture of the filter structure in manufacturing the blood filter device.

First, the filter 8 is mounted in the annular holder 9 as shown in FIG. 10. Then, the auxiliary bonding resin 13 is charged into the space between the outer periphery of the filter 8 and the inner peripheral surface of the annular holder 9 and is hardened, as shown in FIG. 11. As shown in the figures, the auxiliary bonding resin 13 is charged into each of peripheral portions of the filter 8, thereby the filter 8 is bonded to the annular holder 9. Though FIG. 11 is a view observed from the front side, also in the backside, the auxiliary bonding resin 13 is charged similarly into each of peripheral portions of the filter 8. Subsequently, a pair of the annular rib substrates 10 are faced respectively to both the top and the bottom surfaces of the filter 8 as shown in FIG. 12, and are mounted thereon so that the plurality of ribs 10b are inserted respectively between the ridgelines of the plurality of pleats of the filter 8. As the result, the filter structure 12 in which the filter 8, the annular holder 9, and the annular rib substrates 10 are combined is formed as shown in FIG. 3.

By forming the filter structure 12 in this way, an operation for inserting respectively the plurality of ribs 10b into the space between the ridgelines of the plurality of pleats can be carried out very easily in the process of mounting the annular rib substrates 10 on the filter 8. This is because, in the process shown in FIG. 11, the filter 8 is retained in a steady shape by mounting the filter 8 in the annular holder 9, and bonding them with the auxiliary bonding resin 13, and thus the operation for mounting the annular rib substrates 10 can be carried out in that state. As the result, the pleats gaps 8c can be formed surely and easily in the peripheral region of the filter 8.

Next, in order to manufacture the blood filter device, the filter structure 12 formed in the above manner is mounted in the retaining portion inner cylinder 3a of the upper half 1a of the housing shown in FIGS. 8A and 8B. Then, the retaining portion outer cylinder 3b of the lower half 1b of the housing shown in FIGS. 9A and 9B is fit into the retaining portion inner cylinder 3a, thereby obtaining the housing 1 as a single component. Subsequently, the housing 1 in which the filter structure 12 is mounted is placed in a device provided with a potting jig as shown in FIG. 13 so as to carry out potting with a sealing resin.

Figure 13:
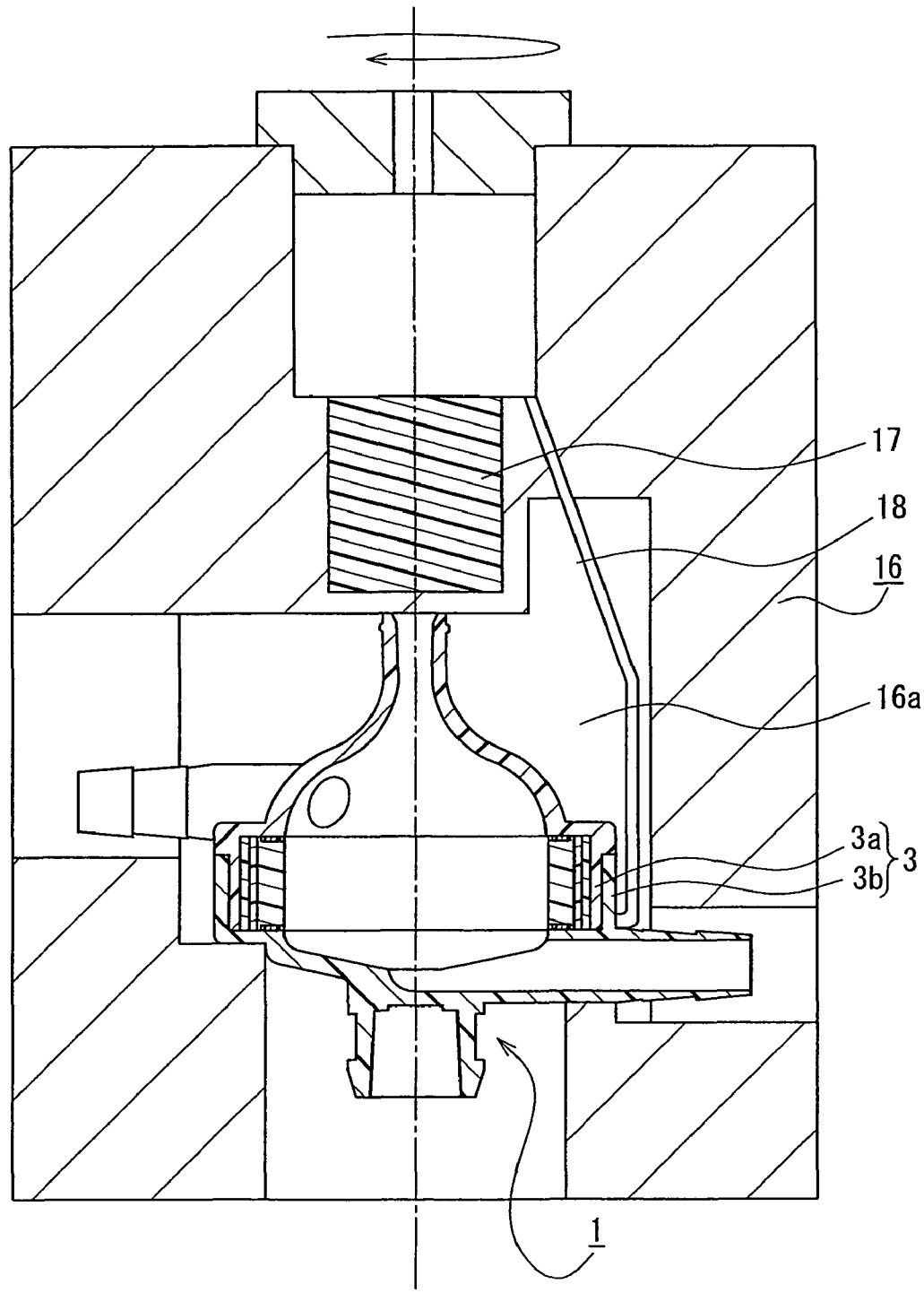
FIG. 13 is a cross-sectional view showing a device used in potting in the manufacturing method.

The device shown in FIG. 13 is composed of a rotating jig 16, a resin reservoir 17, and a resin supply channel 18. The rotating jig 18 includes a cavity 16a having a prescribed shape for supporting the housing 1. The resin reservoir 17 storing a sealing resin such as a urethane resin is provided at the top of the rotating jig 16, and the resin supply channel 18 is formed from the resin reservoir 17 to a side surface of the filter retaining portion 3. By placing the housing 1 in the rotating jig 16 and rotating the rotating jig 16, the housing 1 rotates together. A sealing resin supplied to the side surface of the filter retaining portion 3 enters the cavity of the retaining portion inner cylinder 3a through the notches 14 and the through holes 15 (see FIGS. 8A, 8B, 9A, and 9B).

When the rotating jig 16 is rotated, horizontal centrifugal force about the central axis of the filter retaining portion 3a acts. As a result, the sealing resin spills out of the resin reservoir 17 so as to be supplied to the retaining portion inner cylinder 3a through the resin supply channel 18, so that the resin is charged into the gap between the inner peripheral surface of the retaining portion inner cylinder 3a and an outer peripheral portion of the filter 8. By hardening the charged resin, the filter 8, the annular holder 9, and the annular rib substrates 10 can be retained to the inner peripheral surface of the retaining portion inner cylinder 3a as shown in FIG. 1C.

The range for charging with a resin is adjusted on the basis of the inner periphery of the annular rib substrate 10. The inner periphery of the annular rib substrate 10 is set to coincide with the diameter of the lower end of the inner peripheral surface of the dome 2 and with the diameter of the upper end of the inner peripheral surface of the bottom portion 4. Accordingly, a channel in the filter 8 defined by the bonding resin 11 continues smoothly from the lower edge of the inner peripheral surface of the dome 2 to the upper end of the inner peripheral surface of the bottom portion 4, and thus an excellent channel condition is obtained.

INDUSTRIAL APPLICABILITY

Since the blood filter device of the present invention can remove easily air bubbles remaining or trapped in the filter, it is useful as a component of an artificial heart-lung circuit.

The invention claimed is:

1. A blood filter device comprising:
    a housing that includes a dome provided with a blood inlet and forming an upper part of the housing, a filter retaining portion positioned below the dome and forming a middle part of the housing, and a bottom portion disposed below the filter retaining portion and provided with a blood outlet; and
    a filter mounted in a cavity of the filter retaining portion and partitioning a cavity of the housing into a dome side and a bottom portion side, the filter formed of a sheet-like filter member folded to have a plurality of pleats, and disposed so that ridgelines of the plurality of pleats traverse respectively the cavity of the filter retaining portion in parallel, wherein the blood filter device comprises:

an annular holder disposed to intervene between an inner peripheral surface of the filter retaining portion and an outer peripheral surface of the filter;

an annular rib substrate, which is an annular member including a plurality of ribs that is formed separately from the annular holder, and is disposed on the ridgelines of the plurality of pleats in an outer peripheral region of the filter so that the ribs are inserted respectively between the ridgelines of the plurality of pleats;

an auxiliary bonding resin that bonds an outer periphery of the filter to an inner peripheral surface of the annular holder, positioning the annular rib substrate at an area inside the auxiliary bonding resin, with an interval provided in a radial direction between an outer peripheral edge of the annular rib substrate and an inner peripheral edge of the auxiliary bonding resin; and a bonding resin that is supplied into outer peripheral portions of the filter including the annular holder and the annular rib substrate and bonds the outer peripheral portion of the filter to the filter retaining portion.

2. The blood filter device according to claim 1, comprising a pair of the annular rib substrates is provided, wherein the annular rib substrates are disposed respectively facing the ridgelines of the plurality of pleats of top and bottom surfaces of the filter.

3. A method of manufacturing a blood filter device, the blood filter comprising: a housing that includes a dome provided with a blood inlet and forming an upper part of the housing, a filter retaining portion positioned below the dome and forming a middle part of the housing, and a bottom portion disposed below the filter retaining portion and provided with a blood outlet; and a filter mounted in a cavity of the filter retaining portion and partitioning a cavity of the housing into a dome side and a bottom portion side, the filter being formed of a sheet-like filter member folded to have a plurality of pleats, and disposed so that ridgelines of the plurality of pleats transverse respectively the cavity of the filter retaining portion in parallel, the method comprising:

mounting the filter in an annular holder formed so as to intervene between an inner peripheral surface of the filter retaining portion and an outer peripheral surface of the filter, so that the outer peripheral surface of the filter faces the inner peripheral surface of the annular holder;

supplying an auxiliary bonding resin into outer peripheral portions of the filter so as to bond outer peripheral portions of the filter to an inner peripheral surface of the annular holder with the auxiliary bonding resin;

mounting an annular rib substrate, which is an annular member having a shape and a size to face ridgelines of the plurality of pleats in an outer peripheral region of the filter and is provided with a plurality of ribs that can be inserted respectively between the ridgelines of the plurality of pleats, on the ridgelines of the plurality of pleats of the filter with an interval provided in a radial direction between an outer peripheral edge of the annular rib substrate and an inner peripheral edge of the auxiliary bonding resin, so that the plurality of ribs are inserted respectively between the ridgelines of the plurality of pleats and forming a filter structure in which the filter, the annular holder, and the annular rib substrates are combined;

placing the filter structure in a cavity of the filter retaining portion and mounting thereof in the housing; and supplying a bonding resin into an outer peripheral portion of the filter including the annular holder and the annular rib substrate and hardening the bonding resin so as to bond the filter to the filter retaining portion with the bonding resin.

4. The method of manufacturing the blood filter device according to claim 3, wherein, after the step of mounting the filter in the annular holder, an auxiliary bonding resin is charged into outer peripheral portions of the filter so as to bond outer peripheral portions of the filter to an inner peripheral surface of the annular holder with the auxiliary bonding resin.

5. The method of manufacturing the blood filter device according to claim 3, wherein, after the step of mounting the filter structure in the housing, the bonding resin is charged into an outer peripheral region of the filter including the annular holder and the annular rib substrate while applying a centrifugal force about a central axis of the cavity of the filter holding portion.

6. The blood filter device according to claim 1, wherein the plurality of ribs are inserted respectively between the ridgelines of the plurality of pleats without reaching substantially to opposite ridgelines of the plurality of pleats.

7. The blood filter device according to claim 1, wherein the auxiliary bonding resin is formed independently of formation of the annular holder.

* * * * *